(12) United States Patent
Yoon et al.

(10) Patent No.: US 7,892,729 B1
(45) Date of Patent: Feb. 22, 2011

(54) UNIVERSAL AND DIFFERENTIAL SEROLOGIC ASSAY FOR SWINE INFLUENZA VIRUS

(75) Inventors: Kyoung-Jin Yoon, Ames, IA (US); Wai-Hong Wu, St. Louis, MO (US); Won-Il Kim, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 723 days.

(21) Appl. No.: 11/473,434

(22) Filed: Jun. 23, 2006

Related U.S. Application Data

(60) Provisional application No. 60/693,751, filed on Jun. 23, 2005.

(51) Int. Cl.
*G01N 33/569* (2006.01)
*G01N 33/53* (2006.01)
*C12Q 1/70* (2006.01)

(52) U.S. Cl. .................... 435/5; 435/7.1; 530/300; 530/350

(58) Field of Classification Search .................. 435/5
See application file for complete search history.

(56) References Cited

FOREIGN PATENT DOCUMENTS

EP 0726316 A2 * 8/1996

OTHER PUBLICATIONS

Lonsdale et al., J of Virological Methods 2003 vol. 110, pp. 67-71.*
Tumpey et al., J Clinical Microbiology 2005 vol. 43, No. 2 pp. 676-683.*
de Boer, Arch Virol. 1990 vol. 115, pp. 47-61.*
Direksin et al. J Vet Diagn Invest vol. 14, pp. 169-171.*
De Boer et al., "An ELISA for detection of antibodies against influenza A nucleoprotein in humans and various animal species," *Arch. Virol.* 115: 47-61 (1990).
Kim et al., "Characterization of the humoral immune response of experimentally infected and vaccinated pigs to swine influenza viral proteins," *Arch Virol.*, 151(1):23-36. Epub (2005).
Long et al., "Adaptation and limitations of established hemagglutination inhibition assays for the detection of porcine anti-swine influenza virus H1N2 antibodies," *J. Vet. Diagn. Invest.* 16: 264-270 (2004).
Renshaw, "Influence of Antibody-Mediated Immune Suppression on Clinical, Viral, and Immune Responses to Swine Influenza Infection," *Am. J. Vet. Res.* 36: 5-13 (1975).
Richt et al., "Vaccination of Pigs against Swine Influenza Viruses by Using an NS1-Truncated Modified Live-Virus Vaccine," *Journal of Virology* 80(22): 11009-11018 (2006).
Shafer et al., "Development and Validation of a Competitive Enzyme-Linked Immunosorbent Assay for Detection of Type A Influenza Antibodies in Avian Sera," *Avian Diseases* 42(1): 28-34 (1998).
Webby et al., "Multiple lineages of antigenically and genetically diverse influenza A virus co-circulate in the United States swine population," *Virus Res.* 103: 67-73 (2004).
Webster et al., "Evolution and Ecology of Influenza A Viruses," *Microbiol. Rev.* 56(1): 152-179 (1992).
Yoon et al., "Swine Influenza Virus: Etiology, Epidemiology and Diagnosis," *In: Trends in Emerging Viral Infections of Swine*, Iowa State University Press, Ames, IA. Morella et al., eds., 23-28 (2002).
Zhou et al., "Evaluation of a Competitive ELISA for Detection of Antibodies against Avian Influenza Virus Nucleoprotein," *Avian Dis.* 42(3): 517-522 (1998).

* cited by examiner

*Primary Examiner*—Mary E Mosher
*Assistant Examiner*—Myron G Hill
(74) *Attorney, Agent, or Firm*—Carol Larcher; Larcher & Chao Law Group

(57) ABSTRACT

A universal and differential assay kit for the detection of antibodies to swine influenza virus (SIV) in a biological sample comprising SIV non-structural 1 (NS1) protein and SIV nucleoprotein (NP); a universal and differential assay method for detecting antibodies to SIV in a biological sample comprising assaying the biological sample for the presence of an antibody to SIV NS1 protein and an antibody to SIV NP; primers; and fusion proteins.

6 Claims, No Drawings

SEQUENCE LISTING

```
<160> NUMBER OF SEQ ID NOS: 13

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aagcaaaagc agggaaaata a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agtagaaaca agggtgtttt t                                              21
```

```
-continued

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agcaaaagca gggtagataa t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4 ttcttctttta attgtcatac t                                             21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcaaaagca ggagtttaaa at                                             22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtagaaaca aggagttttt t                                              21

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggaattcatg agtgacatcg aagccatggc gtctc                               35

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccgctcgagt caactgtcat actcctctgc attgtctccg                          40

<210> SEQ ID NO 9
<211> LENGTH: 38
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggaattccat ggattccaac actgtgtcaa gctttcag                         38

<210> SEQ ID NO 10
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtcgactcag tggtggtggt ggtggtgctt ctgctctgga ggtagtgaag gtctccc    57

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aattcccacc accaccacca ccactgac                                    28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcgagtcagt ggtggtggtg gtggtggg                                    28

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
  1               5
```

UNIVERSAL AND DIFFERENTIAL SEROLOGIC ASSAY FOR SWINE INFLUENZA VIRUS

CROSS-REFERENCE TO RELATED PATENT APPLICATIONS

This application claims the benefit of U.S. Provisional Patent Application No. 60/693,751, which was filed on Jun. 23, 2005, and which is hereby specifically incorporated by reference in its entirety.

TECHNICAL FIELD OF THE INVENTION

The present invention relates to a method and kit for a subtype-unrestricted serologic assay for the detection of swine influenza virus in a sample, such as a biological sample from a pig, and for the differentiation of exposed pigs from vaccinated or inoculated pigs.

BACKGROUND OF THE INVENTION

Swine influenza is one of the economically significant acute respiratory diseases in pigs of all ages throughout the world since it was initially recognized in the early 1900's (Shope, J. Exp. Med. 54:373-385 (1931)). Occasionally, the disease is also presented as a reproductive problem in breeding animals at any time of gestation. Because of its economic significance, vaccination of gilts and sows using inactivated vaccines has been commonly practiced to prevent reproductive loss in breeding animals and productivity loss in young pigs due to respiratory disease.

The disease is caused by swine influenza virus (SIV), which is a member of the genus *Influenzavirus* in the family Orthomyxoviridae (Esterday et al., "Swine Influenza." In: Diseases of Swine. Iowa State University Press, Ames, Iowa, Straw et al., eds., 1999, pp. 277-290). SIV contains 8 segmented RNA molecules, each of which encodes for 4 structural proteins (i.e., hemagglutinin (H), neuraminidase (N), nucleoprotein (NP), and matrix (M1 and M2)), and nonstructural proteins (three polymerases (PA, PB1 and PB2) and non-structural (NS) proteins NS1 and NS2). The NP and M1 proteins are internal structural proteins and serve as antigenic determinants for the type (i.e., A, B, or C) of influenza virus as these proteins are antigenically most conserved among the same type. The M2 is transcribed from the M segment through gene splicing, acts as an ion channel, and favors viral entry (Hay, Semin. Virol. 3:21-30 (1992)). The H and N proteins are surface proteins specific for subtypes and play a critical role in viral entry to and release from target cells, respectively. To date, three subtypes of influenza A viruses, such as H1N1, H1N2, H3N1 and H3N2, have been consistently implicated in swine influenza, although 15 and 9 different H and N subtypes, respectively, are known to exist among avian and mammalian influenza viruses (Esterday et al. (1999), supra). The NS1 protein is expressed only during the natural infection and has shown a role in down-regulating the host innate immune response (Palese et al., Arch. Virol. Suppl. 15: 131-138 (1999); and Wang et al., J. Virol. 74: 11566-11573 (2000)), while NS2 protein, which is expressed from the NS1 gene through gene splicing, functions as a Nuclear Export Protein (NEP) for translocation of ribonucleoptroteins (RNPs); (Hilleman, Vaccine 20: 3068-3087 (2002); and O'Neill et al., EMBO J. 17: 288-296 (1998)).

A definitive diagnosis of swine influenza requires the detection of virus or viral antigen in tissues and/or secretions of clinically affected animals. Nonetheless, serological tests, such as hemagglutination inhibition (HI) test, serum-virus neutralization test, indirect fluorescent antibody test, or enzyme-linked immunosorbent assay (ELISA), are often employed to detect animals that have been exposed to the virus because the disease has a very short course and because the causative agent becomes undetectable in infected animals quickly after infection (Yoon et al., Swine Influenza Virus: Evolution, Epidemiology and Diagnosis. In: Trends in Emerging Viral Infections of Swine, Iowa State University Press, Ames, Iowa. Morella et al., eds., 2002, pp. 23-28). Serology is also used to assess the immune status of pigs at various stages within an operation so that the level of herd immunity or timing of vaccination can be determined. The diagnostic value of serologic data, however, is frequently confounded by several factors, such as antigenic difference between the virus that induced the antibody and the virus that was used in the test (Long et al., J. Vet. Diagn. Invest. 16: 264-270 (2004)), and the difficulty in differentiating whether detected antibody is of maternal origin, or was induced by infection or vaccination (Renshaw, Am. J. Vet. Res. 36: 5-13 (1975)).

Until the early 1990's, only classical H1N1 had circulated in U.S. swine populations. Moreover, the HI assay has been most commonly used for serodiagnosis of SIV infection in veterinary diagnostic laboratories in North America because: a) it is relatively inexpensive; b) the antigenicity of SIV in the U.S. swine population has been very stable with respect to the subtype of the implicating virus; and c) results show a relatively good prediction for the immune protection of pigs from subsequent infection. However, such utility and reliability of this subtype-specific assay was recently diminished due to the emergence of new subtypes and new reassortants (e.g., H3N2, H1N2, H3N1, and H9N2; etc.) in U.S. pig populations, as well as progressive antigenic drift within the same subtype (Webby et al., Virus Res. 103: 67-73 (2004); and Webster et al., Microbiol. Rev. 56: 152-179 (1992)).

Accordingly, there remains a need for a subtype-unrestricted universal serologic assay to detect pigs exposed to SIV and, at the same time, preferably differentiate exposed animals from vaccinated animals. It is an object of the present invention to provide materials and a method for such an assay. This and other objects and advantages of the present invention, as well as additional inventive features, will become readily apparent from the detailed description provided herein.

BRIEF SUMMARY OF THE INVENTION

The present invention provides a universal and differential assay kit for the detection of antibodies to SIV in a biological sample, such as from a swine. The kit comprises SIV NS1 protein and SIV NP.

The present invention also provides a universal and differential assay method for detecting antibodies to SIV in a biological sample, such as from a swine. The method comprises assaying the biological sample for the presence of an antibody to SIV NS1 protein and an antibody to SIV NP. The method can further comprise determining if the swine is vaccinated for SIV or exposed to/infected with SIV.

The present invention further provides a pair of primers selected from the group consisting of:

(i) a primer comprising the sequence 5'AAGCAAAAG-CAGGGAAAATAA 3' [SEQ ID NO: 1] and a primer comprising the sequence 5'AGTAGAAACAAGGGTGTTTTT 3' [SEQ ID NO: 2];

(ii) a primer comprising the sequence 5'AGCAAAAG-CAGGGTAGATAAT 3' [SEQ ID NO: 3] and a primer comprising the sequence 5' TTCTTCTTTAATTGTCATACT 3' [SEQ ID NO: 4]; and (iii) a primer comprising the sequence 5'AGCAAAAG-CAGGAGTTTAAAAT 3' [SEQ ID NO: 5] and a primer comprising the sequence 5'AGTAGAAACAAGGAGTTTTTT 3' [SEQ ID NO: 6], wherein each primer can comprise up to 3 additional nucleotides at the 5' end and/or at the 3' end. Accordingly, the present invention also provides a pair of primers selected from the group consisting of:

(i) a primer consisting of the sequence 5'AAGCAAAAG-CAGGGAAAATAA 3' [SEQ ID NO: 1] and a primer consisting of the sequence 5'AGTAGAAACAAGGGTGTTTTT 3' [SEQ ID NO: 2];

(ii) a primer consisting of the sequence 5'AGCAAAAG-CAGGGTAGATAAT 3' [SEQ ID NO: 3] and a primer consisting of the sequence 5' TTCTTCTTTAATTGTCATACT 3' [SEQ ID NO: 4]; and (iii) a primer consisting of the sequence 5'AGCAAAAG-CAGGAGTTTAAAAT 3' [SEQ ID NO: 5] and a primer consisting of the sequence 5'AGTAGAAACAAGGAGTTTTTT 3' [SEQ ID NO: 6].

Also provided are fusion proteins. One fusion protein comprises NS1 and glutathionine-S-transferase (GST). Another fusion protein comprises NP and maltose binding protein (MBP).

DETAILED DESCRIPTION OF THE INVENTION

The present invention provides a universal and differential assay kit for the detection of antibodies to SIV in a biological sample. The kit comprises SIV NS1 protein and SIV NP. The NS1 protein can be part of a fusion protein, such as part of a fusion protein with GST. The NP alternatively or additionally can be part of a fusion protein, such as part of a fusion protein with MBP.

The kit can comprise at least one first vessel, which contains the SIV NS1 protein, optionally as part of a fusion protein, and SIV NP, optionally as part of a fusion protein, and a second vessel containing a first indicator reagent that specifically complexes with an anti-SIV NS1 antibody and a second indicator reagent that specifically complexes with an anti-SIV NP antibody. The SIV NS1 protein and the SIV NP can be contained in separate first vessels. The SIV NS1 protein and the SIV NP can be immobilized on a solid support. The first indicator reagent can comprise a first detectable label, and the second indicator reagent can comprise a second detectable label. In other words, the first and second detectable labels can be the same or different. Preferably, the presence of the detectable labels can be detected in the same manner. The immobilization of proteins on a solid support and the use of indicator reagents, in particular indicator reagents comprising detectable labels, are known in the art.

The present invention also provides a universal and differential assay method for detecting antibodies to SIV in a biological sample. The method comprises assaying the biological sample for the presence of an antibody to SIV NS1 protein and an antibody to SIV NP in a sample (e.g., a biological sample, such as from a swine). Any suitable method of determining the presence of antibodies to SIV NS1 protein and SIV NP can be used in the context of the present invention, as is known in the art. Accordingly, the present invention provides a method for detecting SIV in a biological sample. The method comprises capturing anti-SIV NS1 protein antibodies and anti-SIV NP antibodies in a biological sample by dispensing the biological sample onto a substrate, which comprises SIV NS1 protein, optionally as part of a fusion protein, and SIV NP, optionally as part of a fusion protein, bound thereto, and detecting the captured anti-SIV NS1 antibodies and anti-SIV NP antibodies in the biological sample by dispensing a first indicator reagent, which specifically complexes with anti-SIV NS1 antibodies, and a second indicator reagent, which specifically complexes with anti-SIV NP antibodies, onto the substrate. When the biological sample is from a swine, the method can further comprise determining if the swine is vaccinated for SIV or exposed to/infected with SIV. While vaccinated swine have antibodies to NP, infected swine have antibodies to NP and NS1.

Viral antigen candidates for use in a serologic assay, whose performance is not restricted by virus subtype, i.e., more sensitive, and which, at the same time, can differentiate vaccinated animals from exposed ones, were identified by characterizing the viral protein specificity of antibody responses in pigs infected by or vaccinated for SIV using Western immunoblotting. As shown in Tables 1 and 2, both IgM and IgG antibody responses of experimentally infected pigs were initially (7 DPI) directed to hemagglutinin, NP, and NS1 and NS2 proteins of SIV, regardless of subtype of the inoculum, and IgG responses were detected by the end of the study (28 DPI). In comparison, IgG antibodies specific for neuraminidase and M1 were first detected late on day 14, and no IgM antibody was detected during the study. In vaccinated pigs, as shown in Tables 3 and 4, no NS1 antibody was detected, while antibody responses to other proteins were identical with those in exposed pigs.

As shown in Table 1, Western blot (WB) analysis of sera from experimentally infected pigs demonstrated a dominant antibody response to NP protein and H protein of each subtype during a 4-week period after inoculation, regardless of the subtype of the challenge virus. Accordingly, NP of SIV was identified as a suitable viral antigen for a universal serologic assay, which overcomes the species specificity of the assays for influenza viruses as several previous studies reported that antibody response against NP protein was consistent across species and among the same types (De Boer et al., Arch. Virol. 115: 47-61 (1990); Shafer et al., Avian Dis. 42: 28-34 (1998); and Zhou et al., Avian Dis. 42: 517-522 (1998)).

TABLE 1

Appearance of swine influenza viral protein-specific antibodies in pigs experimentally inoculated with H1N1 or H3N2 SIV as determined by WB analysis.

| Antibody Isotype | SIV Protein | Days Post-Infection | | | |
|---|---|---|---|---|---|
| | | 0 | 7 | 14 | 18 |
| IgM | H1 | 0/0$^a$ | 6/0 | 2/0 | 0/0 |
| IgM | H3 | 0/0 | 0/6 | 0/6 | 0/4 |
| IgM | N1$^b$ | 0/0 | 0/0 | 0/0 | 0/0 |
| IgM | N2$^b$ | 0/0 | 0/0 | 0/0 | 0/0 |
| IgM | NP$^b$ | 0/0 | 6/6 | 2/6 | 2/6 |
| IgM | M1 | 0/0 | 0/0 | 0/0 | 0/0 |
| IgM | NS1$^b$ | 0/0 | 6/6 | 6/6 | 2/6 |
| IgM | NS2$^b$ | 0/0 | 6/6 | 6/6 | 2/6 |
| IgG | H1 | 0/0 | 2/0 | 6/0 | 6/0 |
| IgG | H3 | 0/0 | 0/2 | 0/6 | 0/6 |
| IgG | N1$^b$ | 0/0 | 0/0 | 6/0 | 6/0 |
| IgG | N2$^b$ | 0/0 | 0/0 | 0/6 | 0/6 |
| IgG | NP$^b$ | 0/0 | 6/6 | 6/6 | 6/6 |
| IgG | M1 | 0/0 | 0/0 | 6/4 | 6/6 |

TABLE 1-continued

Appearance of swine influenza viral
protein-specific antibodies in pigs
experimentally inoculated with H1N1 or
H3N2 SIV as determined by WB analysis.

| Antibody Isotype | SIV Protein | Days Post-Infection | | | |
|---|---|---|---|---|---|
| | | 0 | 7 | 14 | 18 |
| IgG | NS1[b] | 0/0 | 6/6 | 6/6 | 6/6 |
| IgG | NS2[b] | 0/0 | 6/6 | 6/6 | 6/6 |

[a]The number of pigs (H1N1/H3N2 infected) seropositive for the given viral protein at the given day post inoculation.
[b]Antibody response to each of the given proteins was assessed with recombinant proteins.

TABLE 2

| Antibody Isotype | SIV Protein | Days Post-Infection | | | |
|---|---|---|---|---|---|
| | | 0 | 7 | 14 | 28 |
| IgM | H | − | + | + | +/− |
| | N | − | − | − | − |
| | NP | − | + | + | +/− |
| | M | − | − | − | − |
| | NS1 | − | + | + | +/− |
| | NS2 | − | + | + | +/− |
| IgG | H | − | +/− | + | + |
| | N | − | − | + | + |
| | NP | − | + | + | + |
| | M | − | − | + | + |
| | NS1 | − | + | + | + |
| | NS2 | − | + | + | + |

The lack or delay of antibody response to M1 protein in exposed or vaccinated pigs was an unexpected observation, since M1 protein is known to be abundant in the influenza virion and also antigenically conserved among the same type of influenza viruses. This observation suggested that an assay using M1 protein may not be as sensitive as an assay using NP protein, since the delayed detection of antibody response to SIV would be expected. Furthermore, as illustrated in Table 3, seroconversion to SIV might not be detected in vaccinated animals. Moreover, the antibody response to M1 protein seemed to vary among strains.

TABLE 3

Appearance of swine influenza viral protein-specific antibodies in pigs
vaccinated with a commercially available, inactivated bivalent SIV
vaccine as determined by WB analysis.

| Antibody Isotype | SIV Protein | Days Post-Infection | | |
|---|---|---|---|---|
| | | 0 | 14 | 28 |
| IgM | H1 & H3[a] | 0/5[b] | 0/5 | 0/5 |
| IgM | N1 & N2[a,c] | 0/5 | 0/5 | 0/5 |
| IgM | NP[c] | 0/5 | 0/5 | 0/5 |
| IgM | M1 | 0/5 | 0/5 | 0/5 |
| IgM | NS1[c] | 0/5 | 0/5 | 0/5 |
| IgM | NS2[c] | 0/5 | 0/5 | 0/5 |
| IgG | H1 & H3[a] | 0/5 | 0/5 | 0/5 |
| IgG | N1 & N2[a,c] | 0/5 | 0/5 | 0/5 |
| IgG | NP[c] | 0/5 | 5/5 | 5/5 |
| IgG | M1 | 0/5 | 0/5 | 0/5 |
| IgG | NS1[c] | 0/5 | 0/5 | 0/5 |
| IgG | NS2[c] | 0/5 | 0/5 | 0/5 |

[a]Antibody responses to both subtypes were identical.
[b]The number of pigs seropositive for the given viral protein/the total number of pigs tested at the given day post-inoculation.
[c]Antibody response to each of the given proteins was assessed with recombinant proteins.

TABLE 4

| Antibody Isotype | SIV Protein | Days Post-Vaccination | | |
|---|---|---|---|---|
| | | 0 | 14 | 28 |
| IgM | H | − | − | − |
| | N | − | − | − |
| | NP | − | + | + |
| | M | − | − | − |
| | NS1 | − | − | − |
| | NS2 | − | − | − |
| IgG | H | − | − | + |
| | N | − | − | − |
| | NP | − | + | + |
| | M | − | − | − |
| | NS1 | − | − | − |
| | NS2 | − | − | − |

Antibodies to NS1 and NS2 proteins were detected only in sera from pigs experimentally infected but not from vaccinated animals. In general, nonstructural proteins of viruses are expressed only during viral replication; hence, nonstructural proteins have the potential to be suitable antigens for differentiating animals vaccinated with a killed product from ones naturally exposed. Influenza virus expresses two non-structural proteins (i.e., NS1 and NS2) besides polymerases in virus-infected cells. Two proteins are encoded by the same genomic RNA molecule (NS segment) but expressed from two different RNA transcripts, which are produced by gene splicing, resulting in distinct differences in the antigenicity and size of NS1 and NS2 proteins. While NS2 protein is a part of the virion, NS1 protein stays in infected cells and plays a role as a true non-structural protein in suppressing host immunity. Although the duration of NS1 antibody in infected pigs could not be determined due to early termination of the study, it would be expected to be relatively long as the antibody titer to NS1 protein continued to increase by day 28 PI based on the intensity of band to NS1 protein on immunoblot membrane. Overall, an early and expectedly long-lasting immune response of infected pigs to NS1 protein favors this protein being used as a differentiation marker between naturally exposed and vaccinated pigs.

Thus, NP and NS1 proteins are suitable antigens for use in a subtype-unrestricted universal serodiagnostic assay, which can differentiate vaccinated animals from infected ones under the current vaccination practice for SIV (e.g., using killed products), which can play a major role in the control of SIV by providing a compatible diagnostic assay even with the emergence of new SIV subtypes.

Based on WB analysis of antibody responses of pigs to SIV infection and vaccination, discussed above, NP and NS1 protein were selected as antigens, and the corresponding genes were used for cloning and expression as a MBP- or GST-fusion protein. The format of the test chosen, in this particular embodiment, was indirect enzyme-linked immunosorbent assay (iELISA). An ELISA kit using selected recombinant antigens of SIV for serodiagnosis of pigs infected with a wild-type of SIV (influenza A viruses) was used, and the performance of the ELISA was evaluated using sera from pigs experimentally infected with SIV of H1N1 or H3N2 subtype and from pigs vaccinated with commercial killed vaccine products, as described more fully in Example 2 below. While all infected pigs were seropositive for NP and NS1 with increasing antibody titers in a time-dependent manner, vaccinated pigs were positive only for NP. Accordingly, an ELISA assay using NP and NS1 proteins can be used as a test for SIV that differentiates infected from vaccinated animals.

Moreover, as illustrated below in Example 2, the kit or ELISA used in the context of the present invention is not restricted to any particular subtype of virus, since the kit or ELISA comprises the NP of SIV, which is antigenically conserved among all influenza A viruses and which is highly immunogenic. The antibody response of swine to infection and vaccination is well-directed to this protein at the early stage as well as the later stage. Moreover, the kit or ELISA comprises NS1 for differential detection of exposed animals from vaccinated animals, as the NSI antigen is expressed only in swine exposed to infectious SIV but not in pigs vaccinated with inactivated virus. Thus, an assay kit can comprise an antibody, such as one or more monoclonal antibodies, or a polyclonal antibody. Accordingly, an assay method can comprise assaying a biological sample for the presence of NS1 protein, optionally as part of a fusion protein. The presence of NS1 protein in a biological sample from a swine indicates that the swine has been exposed to infectious SIV, not vaccinated with inactivated virus. Manipulation of target genes to minimize cross-reactivity and determination of ordinary antigen solubility for appropriate coating of the antigen on a solid surface are within the ordinary skill in the art.

As is understood by those of skill in the art, the antigens used in the context of the present invention can be prepared using any suitable recombinant DNA, RNA, and/or polypeptide methodology. Moreover, any suitable method for production and use of the antigens, polynucleotides, polypeptides, antibodies, detectable labels, such as fluorescent markers, and other molecules and moieties, including assaying methods and other methodologies, can be used in the context of the present invention (see, e.g., Molecular Cloning: A Laboratory Manual, Joseph Sambrook, David W. Russell, Cold Spring Harbor Press (2001); High Throughput Screening: Methods and Protocols (Methods in Molecular Biology, 190), William P. Janzen, Humana Press (2002); Antibody Engineering: Methods and Protocols (Methods in Molecular Biology), Benny K. C. Lo, Human Press (2004); and Using Antibodies: A Laboratory Manual, Edward Harlow, David Lane, Cold Spring Harbor Press (2001)). Examples of suitable detectable labels that can be used in the context of the present invention include, but are not limited to, a fluorophore, a chromophore, a radionuclide, biotin, digoxigenin, SAMSA, or other fluorescent marker (e.g., quantum dot), as is understood by those of ordinary skill in the art.

EXAMPLES

The following examples serve to illustrate the present invention. The examples are not intended to limit the scope of the invention in any way.

Example 1

Viruses and cell: Two field isolates of SIV were used for the study. One isolate was designated A/Swine/IA/40776/92 (classical H1N1), and the other one was designated A/Swine/IA/41305/98 (H3N2, cluster I). Both viruses were isolated from pigs in commercial hog operations undergoing severe respiratory disease. Initial virus isolation attempts were made using 9- to 10-day-old embryonating eggs (Dowdle, et al., "Laboratory propagation of human influenza viruses, experimental host range, and isolation from clinic material." In: The Influenza Viruses and Influenza, Academic Press, New York, N.Y. Kilbourne, ed., 1975, pp. 243-268). Experimentally, the ability of the isolates to cause flu-like respiratory disease has been reproduced (Janke et al., Proceeding(s) of the 44th Annual Meeting of the American Association of Veterinary Laboratory Diagnosticians, Hershey, Pa., 2001, p. 30; and Vincent et al., Proceedings of the 40th Annual Meeting of the American Association of Veterinary Laboratory Diagnosticians, Louisville, Ky., 1997, p. 38).

The Madin-Darby Canine Kidney (MDCK) cell was used to propagate the viruses (Tobita et al., Med. Microbiol. Immunol. 162: 9-14 (1975)). Monolayers of MDCK cells were prepared in Minimum Essential Medium (MEM, Sigma, St. Louis, Mo., USA) supplemented with 10% fetal bovine serum (FBS, Sigma), 20 mM L-glutamine, 100 IU/ml penicillin, 100 µg/ml streptomycin, 50 gentamicin, and 0.25 µg/ml amphotericin B (hereafter, MEM-GM) at 37° C. in a water-jacketed $CO_2$ incubator. Before inoculating the virus, cell monolayers were rinsed with Earle's Balanced Salt Solution (EBSS, Sigma) containing 0.2 µg/ml of TPCK-treated trypsin (Worthington, Lakewood, N.J., USA), 100 IU/ml penicillin, 100 µg/ml streptomycin, 50 µg/ml gentamicin, and 0.25 µg/ml amphotericin B (hereafter, EBSS-trypsin). Then, the cells were inoculated with 1 hemagglutination (HA) unit of one of the two viruses and incubated for 2 hrs at 37° C. in the incubator. At the completion of incubation, the cells were rinsed three times with EBSS-trypsin, which was substituted with MEM-GM supplemented with 0.5% bovine serum albumin (BSA, Sigma), instead of FBS. However, BSA was removed from the cell culture medium when preparing the virus and viral antigens for Western immunoblot as BSA was found to block antibody detection of viral proteins, particularly HA and NA proteins, during preliminary study. After 24- to 36-hr further incubation at 37° C. in the incubator, each virus was harvested, and the virus titer of each preparation was determined by HA assay.

Serum samples and reference antibodies: Known positive serum samples (n=18) for H1N1 were collected from a group of 6 young crossbred pigs, which were experimentally inoculated with H1N1 SIV (IA92) via nebulization of 2 ml of homogenate of lungs collected from gnotobiotic pigs infected with the virus. In addition, 18 serum samples were obtained by sequential bleedings from 6 pigs exposed to H3N2 SIV (IA98) in the identical manner and used as known positive sera for H3N2. All animals were bled on days 0, 7, 14, and 28 post-inoculation (PI).

Known negative serum samples (n=18) consisted of day 0 serum samples from the 12 pigs described above and sera collected in the identical manner from 6 sham-inoculated control pigs in the studies described above.

To get vaccine antibody, 5 pigs were vaccinated with a commercial bivalent (i.e., H1N1 and H3N2) SIV vaccine (End-FLUence®, Intervet, Grand Island, N.Y., USA; and other vaccines) by intramuscular (IM) injection two times at two weeks apart as recommended by the manufacturer. The sera were collected at two weeks after the first vaccination and at two weeks after the second vaccination (i.e., four weeks after the first vaccination).

H1N1 and H3N2 hyperimmune pig sera were purchased from the National Veterinary Services Laboratories (NVSL), Ames, Iowa, USA and used as reference. Those sera were produced against a classic H1N1 SIV isolate (A/Sw/IA/73) or cluster I H3N2 isolate (A/Sw/TX/98) (Webby et al., J. Virol. 74: 8243-8251 (2000)), respectively, in gnotobiotic pigs.

Besides swine sera, murine monoclonal antibodies specific for M1 protein of a H3N2 human influenza virus (ViroStat, Portland, Me., USA) were also employed for the study as additional reference.

Preparation of crude viral antigen: when a cytopathic effect was evident in approximately 50% of the monolayer, the flasks were subjected to one cycle of freeze-thawing at −80° C./37° C., and the cells and supernatant were pelleted by ultracentrifugation for 3 hrs at 100,000×g. The resulting pellet was resuspended in 500 µl of Tris lysis buffer (10 mM Tris, 0.04% CHAPS, 0.15 M NaCl, 0.0001% aprotinin and 1 mM EDTA), pH 8.0, and incubated overnight at 4° C. with gentle stirring, then stored at −80° C. Mock-infected cells were prepared in the identical manner and used as cell control antigen. Protein concentration was determined with DC™ Protein Assay (Bio-Rad, Hercules, Calif., USA).

Preparation of recombinant SIV antigens: To construct baculovirus expression vectors containing NS1, NP, N1 or N2 genes, the specific cDNA was first amplified from SIV genomic RNA by a reverse transcription polymerase chain reaction (RT-PCR). The H1N1 SIV was the donor of the NS, NP and N1 genes, and H3N2 SIV was the donor of the N2 gene. Each PCR product was sequenced for verification, and then cloned into the plasmid vector pGEM-T-easy (Promega, Madison, Wis., USA). The sequences of the PCR primers were:

NS-forward-5'AAGCAAAAGCAGGGAAAATAA 3' [SEQ ID NO: 1];

NS-reverse-5'AGTAGAAACAAGGGTGTTTTT 3' [SEQ ID NO: 2];

NP-forward-5'AGCAAAAGCAGGGTAGATAAT 3' [SEQ ID NO: 3];

NP-reverse-5' TTCTTCTTTAATTGTCATACT 3' [SEQ ID NO: 4];

N1 and 2-forward-5'AGCAAAAGCAGGAGTTTAAAAT 3' [SEQ ID NO: 5]; and

N1 and 2-reverse-5'AGTAGAAACAAGGAGTTTTTT 3' [SEQ ID NO: 6].

Each PCR product in the pGEM-T-easy vector and the baculovirus protein expression plasmid pFastBac1 were digested by restriction enzymes, electrophoresed on an agarose gel, purified, and ligated with each other using restriction enzyme sites. The NS fragment was digested with SalI and SphI, NP and N2 were digested with EcoRI and SpeI, and N1 was digested with EcoRI and XbaI, respectively. Then each digested fragment was inserted into a corresponding site of pFastBac1 (Invitrogen, Carlsbad, Calif., USA). After transformation, pFBNS, pFBNP, pFBN1 and pFBN2, which were used to express NS, NP, N1 and N2, respectively, in the baculovirus expression system, were cloned. DNA sequence analysis was used to confirm the authenticity of each plasmid construct. The pFBNS, pFBNP, pFBN1 and pFBN2 were then individually transformed into DH10BacTM, and recombinant baculoviruses AcNS, AcNP, AcN1, and AcN2 were constructed by transposition into AcMNPV genomic DNA according to the manufacturer's instructions ("BAC-TO-BAC™" manual, Invitrogen). Recombinant viruses were inoculated in Sf-9 insect cells (Invitrogen) and propagated for 4 days. The cells were then lysed in Tris lysis buffer and used for SDS-PAGE after protein concentration of each preparation was determined.

In view of the above, the present invention also provides a pair of primers. The primers can be selected from the group consisting of:

(i) a primer comprising the sequence 5'AAGCAAAAGCAGGGAAAATAA 3' [SEQ ID NO: 1] and a primer comprising the sequence 5'AGTAGAAACAAGGGTGTTTTT 3' [SEQ ID NO: 2];

(ii) a primer comprising the sequence 5'AGCAAAAGCAGGGTAGATAAT 3' [SEQ ID NO: 3] and a primer comprising the sequence 5' TTCTTCTTTAATTGTCATACT 3' [SEQ ID NO: 4]; and (iii) a primer comprising the sequence 5'AGCAAAAGCAGGAGTTTAAAAT 3' [SEQ ID NO: 5] and a primer comprising the sequence 5'AGTAGAAACAAGGAGTTTTTT 3' [SEQ ID NO: 6], wherein each primer can comprise up to 3 additional nucleotides at the 5' end and/or at the 3' end, is also provided. Accordingly, provided is a pair of primers selected from the group consisting of:

(i) a primer consisting of the sequence 5'AAGCAAAAGCAGGGAAAATAA 3' [SEQ ID NO: 1] and a primer consisting of the sequence 5'AGTAGAAACAAGGGTGTTTTT 3' [SEQ ID NO: 2];

(ii) a primer consisting of the sequence 5'AGCAAAAGCAGGGTAGATAAT 3' [SEQ ID NO: 3] and a primer consisting of the sequence 5' TTCTTCTTTAATTGTCATACT 3' [SEQ ID NO: 4]; and (iii) a primer consisting of the sequence 5'AGCAAAAGCAGGAGTTTAAAAT 3' [SEQ ID NO: 5] and a primer consisting of the sequence 5'AGTAGAAACAAGGAGTTTTTT 3' [SEQ ID NO: 6]. It will be understood by one of ordinary skill in the art that one up to a few, such as 1, 2 or 3, nucleotides in the above sequences can be modified, such as by substitution, and the primers will still function.

HI test: Antibody response of the animals was assessed by HI test using a standard protocol based on the procedure recommended by the Centers for Disease Control (Concepts and procedures for laboratory-based influenza surveillance. Centers for Disease Control, U.S. Department of Health and Human Services, Washington, D.C. (1982)). Each sample was tested for its HI activity against H1 and H3 SIV. The HI antibody titer of each sample was determined as the reciprocal of highest dilution in which no HA was observed. Samples with no HI activity at 1:10 dilution were considered negative for HI antibody.

SDS-PAGE and WB: Viral and cellular or recombinant proteins were electrophoretically separated on vertical 12% polyacrylamide slab gels under non-reducing conditions and electrotransferred to nitrocellulose membranes (Bio-Rad). In brief, each viral antigen, cellular antigen or recombinant protein preparation was mixed with 5× sample buffer containing 0.6 M Tris-HCl (pH 6.8), 25% glycerol, 2% SDS and 0.1% bromophenol blue, and incubated for 5 min at 65° C. (Epand et al., Biochem. J. 365: 841-848 (2002)) or 5 min at 100° C. for recombinant proteins. Then 100 μl of each sample were loaded on each gel and electrophoresed for 80 min at the constant voltage of 100 along with pre-stained molecular weight markers (Bio-Rad). After electrophoresis, polypeptides and the markers separated on each gel were electrotransferred onto a 0.2 μM nitrocellulose membrane overnight at 30 volts under refrigerated conditions. Each membrane was blocked with a 1% skim milk solution by submerging the membrane in the solution for 30 min at ambient temperature. Each membrane was then cut into 0.5 cm-wide strips, dried at ambient temperature, and stored frozen until use.

For WB analysis, a pair of strips (one with viral antigen and the other with cellular antigen) was incubated with each serum sample diluted 1:50 in 20 mM Tris-buffered saline solution with 0.05% Tween 20 (TBST, pH 7.5) for 90 min at ambient temperature with slow rocking, and then rinsed at least 3 times using TBST. Each pair of strips was incubated with goat anti-swine IgG or IgM labeled with peroxidase (Kirkegaard-Perry Laboratories, Gaithersburg, Md., USA) for 60 min at ambient temperature. Then, antigen-antibody reactions were visualized by adding TMB substrate (Kirkegaard-Perry Laboratories) to each strip and incubated for up to 5 min at ambient temperature. Colorimetric reaction was stopped by rinsing the strips with distilled water.

HI antibody responses to infection and vaccination: All inoculated animals had HI antibody only to the respective subtype of SIV inoculum on day 7 PI. Antibody titers ranged from 1:320 to 1:640. All pigs were still seropositive (1:160-1:320) at the termination of the study (4 weeks PI), although HI antibody levels gradually declined after 7 days PI.

All vaccinated animals were positive for HI antibody against SIV of both subtypes (i.e., H1 and H3). HI titers induced by vaccination were not detected on 2 weeks after the first vaccination but on 2 weeks after second-dose vaccination, ranging from 1:128 to 1:240.

Protein profile of SIV: Three distinct viral polypeptides were visualized from SIV-infected cell lysate using the hyperimmune polyclonal anti-SIV reference sera, each of which was determined to be H, N, NP, or M1, respectively, based on their observed molecular mass, electrophoretic pattern similar to that of recombinant NP and N proteins, and/or reactivity to monoclonal antibodies specific for M1 protein.

The apparent molecular mass of H protein of both H1N1 and H3N2 SIV was estimated to be 82 kDa under a non-reducing condition. Each of the hyperimmune H1N1 and H3N2 reference sera recognized the H protein in a subtype-specific manner. The molecular mass of N and NP proteins was, however, indistinguishable by WB, even when baculovirus recombinant N and NP proteins were used as antigens. The estimated molecular size of both proteins was approximately 58 kDa, although the size of N and NP proteins was expected to be 50 and 55 kDa, based on their deduced amino acid sequences, respectively. The N subtype specificity of each reference hyperimmune serum was clearly demonstrated using recombinant N proteins.

The molecular mass of M1 protein was estimated to be 30 kDa. The H1N1 reference hyperimmune serum cross-reacted with M1 protein of both subtypes as with NP. In contrast, the H3N2 reference serum used in this study appeared to have no to a lower level of antibody specific for M1 protein, based on the intensity and absence of the band specific for M1 protein on the membrane. Since the H1N1 reference serum and M1 protein-specific monoclonal antibody demonstrated the presence of M1 protein in both SIV antigen preparations, no or weak reactivity with M1 protein by the H3N2 reference serum was not attributed to the difference in the protein amount between the two viral antigen preparations.

Two proteins were expressed from the same NS gene, which was due to internal splicing of mRNA. The smaller protein was considered to be NS2, rather than degraded NS1 products, since only NS1 protein was expressed from the NS gene cloned into a prokaryotic system and the molecular size of the smaller protein was identical with that calculated from the amino acid sequence of NS2. The molecular mass of NS1 and NS2 proteins was estimated to be 28 kDa and 17 kDa, respectively. The amount of NS1 and NS2 proteins present in the crude viral antigen preparation appeared to be lower than the detection limit of WB as the reference sera recognized the proteins only when recombinant NS protein was employed.

WB analysis of antibody responses to SIV infection: Viral protein specificity of antibody responses in experimentally infected pigs as determined by WB is summarized in Table 1. Antibody response of the infected pigs to the viral surface proteins, i.e., H and N, was subtype-specific. IgM antibody against H protein was detected in all pigs on day 7 PI. Based on the intensity of the band, the level of IgM antibody to H protein started to decrease after 14 days PI. IgG antibody specific for H protein was, on the other hand, detected in all pigs on day 14 PI, although weak IgG antibody response to H protein initially appeared on day 7 PI in some of the pigs, and continued to be present until the last sampling day (i.e., 28 days PI). In comparison, no IgM antibody against N protein was detected in any of the inoculated pigs during the study period (28 days PI), whereas IgG antibody specific for N protein was detected on day 14 PI in all animals and thereafter until the termination of the study.

Antibody responses to the internal proteins, such as NP and M1, were independent of the subtype of each SIV inoculum. IgG antibody response of the inoculated pigs to M1 protein was delayed until 14 days PI. No pigs developed detectable IgM antibody specific for M1 protein during the study period. In comparison, both IgG and IgM antibodies against NP protein were detected in all inoculated pigs on day 7 PI. NP-specific IgG antibody persisted in all pigs until the end of the study.

Antibody responses to NS1 and NS2 proteins were also independent of the subtype of SIV given. Both IgM and IgG antibodies specific for NS1 and NS2 recombinant proteins were detected in all inoculated pigs on day 7 PI. IgG antibody was continued to be detected until 28 days PI, while IgM response diminished over time and was very weak on day 28 PI.

WB analysis of antibody responses to SIV vaccination: Viral protein specificity of antibody response in pigs vaccinated with a bivalent killed product is summarized in Table 2. Antibody response of the vaccinated animals to the surface proteins of SIV was directed mainly against H protein after 2 doses of the vaccine. While no IgM antibody specific for H protein was detected in any of the sera collected after a 2-dose vaccination, H protein-specific IgG antibody was detected in the animals at 2 weeks after the second dose but not after the first dose. In contrast, no IgM and IgG antibodies specific for N protein were apparent, even if the sera were tested on both native and recombinant N proteins.

Weak reactivity of antibody to the internal proteins (i.e., NP and MD was observed by WB when crude viral antigen was used. When recombinant NP was employed, both IgM and IgG antibodies specific for NP protein were detected in all vaccinated pigs at 2 weeks after the first vaccination, even though IgG response was rather weak. NP-specific IgG antibody increased in intensity after the second vaccination. With respect to nonstructural proteins, neither IgM nor IgG antibody against NS1 and NS2 proteins was detected in any of the sera collected from vaccinated pigs during the study period.

Example 2

Method and Materials: Two "challenge" viruses were used for the study: H1N1 (A/SW/IA/92) and H3N2 A/SW/IA/98). Two HI1 assay reference viruses were used: H1N1 (A/SW/IA/73) and H3N2 (A/SW/IA/98). The MDCK cells were used to propagate the viruses, as described above in Example 1.

Challenged Serum Samples: Ten (10) and twelve (12) pigs were challenged with H1N1 and H3N2, respectively, and eleven (11) pigs were used for negative control. Bleeding was performed at 0, 1, 2 and 3 or 4 weeks after challenge.

Negatives: All sera on day 0 and from sham-inoculated controls pigs (n=85).

Positives: Serum samples were collected from infected pigs (n=99).

Vaccinated Serum Samples: Seventy-four (74) pigs were inoculated twice (3 weeks apart) with one of two commercial bivalent vaccines, and bled at 7 days after the 2nd vaccination (28 days after 1st vaccination).

UdELISA: Test antigens used in the universal differential ELISA (UdELISA) assay were: rNP (as MBP fusion protein);

and rNS-1 (as GST fusion protein) with 6×His tag (6×His tag disclosed as SEQ ID NO: 13) at the C terminus. Control antigens used in the present assay were: rMBP and rGST-6× His (6×His tag disclosed as SEQ ID NO: 13). Purified antigen was coated overnight at 4° C., and blocking was performed using 1×PBS containing 10% (w/v) skim milk incubation was performed with pig sera (primary Ab), and detection of bound primary Ab was performed with HRP goat anti-swine IgG or IgM 2nd Ab OD at 450 nm.

The UdELISA (NP) assay detected pigs infected with both H1N1 and H3N2 (i.e., not restricted to the subtype). The UdELISA method appeared to be as sensitive as commercial H1N1 ELISA at a late time-point of infection (28 days PI). Moreover, the UdELISA assay provided sensitive detection of infected pigs at early time points of the infection. The UdELISA (NS-1) can also differentiate vaccinated pigs from infected pigs. In particular, while the NS1 antibody also was not induced by vaccination with commercial vaccines, and no significant difference was detected in ELISA values between vaccinated and unvaccinated pigs (P>0.05), a significant difference (p<0.0001) in the level of anti-NS antibody was observed between infected and vaccinated animals when tested with the UdELISA assay.

Example 3

Virus, animals and serum samples: Two strains of H1N1 (typical H1N1: A/Sw/IA/40776/92; atypical: a/Sw/NE/9069/92) and 2 strains of H3N2 (A/Sw/IA/41305/98 and A/Sw/NC/35922/98) were used in this study for infection. The pathogenicity of swine influenza viruses to swine was demonstrated previously (Janke et al., Proc. 44$^{th}$ Ann. Mtg. Amer. Assoc. Vet. Lab. Diag., Hershey, Pa. (2001), p. 30; Vincent et al., Proc. 40$^{th}$ Ann. Mtg. Amer. Assoc. Vet. Lab. Diag., Louisville, Ky. (1997), p. 38; and Yoon et al., J. Vet. Diag. Invest. 16: 197-201 (2004)).

Pigs used in this study were 4-week-old, large, white, young animals from herds free of PRRSV and SIV. The animals were tested by HI and ELISA for SIV and PRRSV, respectively, before and upon arrival. Before infection, all animals showed normal body temperature and had no clinical sign of respiratory disease. Infections were done through nebulization of 2 ml of homogenate of lung tissues collected from gnotobiotic pigs infected with the viruses. Each ml of homogenate contains SIV at a titer of 5×10$^{10}$ egg infectious dose (EID). Two different commercial SIV bivalent vaccines were used in this study. Vaccinated animals were immunized with one of these vaccines through two intramuscular injections at a 3-week interval.

Serum panels composed of positive sera (n=99) were collected from pigs infected with SIV (H1N1 or H3N2); negative sera (n=87) were collected from pigs never exposed to SIV; and vaccinated sera (n=74) were collected from pigs vaccinated with either one of the two commercial bivalent SIV vaccines. Positive, negative or vaccinated sera were selected from these serum panels and tested with the UdELISA, HI assay, and the commercial indirect SIV ELISA kit (H1N1 or H3N2 kit). Positive and negative serum samples represent different sampling points (0, 1, 2 and 3 or 4 weeks PI) after experimental inoculation and were used for a time-series analysis of sensitivity. All serum samples from experimental animals were obtained from other researchers at ISU and NADC and biologic firms through collaboration.

Plasmid construction: The antigens used for the UdELISA were NP and NS1 protein (Genus: *Influenzavirus* A) of a swine influenza virus (A/SW/IA/92) of H1N1 subtype. The SIV cDNA of the protein coding regions of NS1, along with 6× histidine carboxylterminus (6×His tag disclosed as SEQ ID NO: 13), and NP were amplified by PCR from NP and NS1 plasmid clones pFBNS and pFBNP (Kim et al., Arch Virol. 151: 23-36 (2006)), respectively, with the following primer sets:

For NP PCR: 92NPF 5'-GGA ATT CAT GAG TGA CAT CGA AGC CAT GGC GTC TC-3' [SEQ ID NO: 7] and 92NPXHOR5'-CCG CTC GAG TCA ACT GTC ATA CTC CTC TGC ATT GTC TCC G-3' [SEQ ID NO: 8].

For NS1 PCR: GEXNS1F 5'-GGA ATT CCA TGG ATT CCA ACA CTG TGT CAA GCT TTC AG-3' [SEQ ID NO: 9] and NS16Hsa1R 5'-GTC GAC TCA GTG GTG GTG GTG GTG GTG CTT CTG CTC TGG AGG TAG TGA AGG TCT CCC-3' [SEQ ID NO: 10].

As control, complementary oligonucleotides 5'-AAT TCC CAC CAC CAC CAC CAC CAC TGA C-3' [SEQ ID NO: 11] and 5'-TCG AGT CAG TGG TGG TGG TGG TGG TGG G-3' [SEQ ID NO: 12] were hybridized to obtain the 6× histidine coding region (6×His tag disclosed as SEQ ID NO: 13) with a stop codon and then inserted downstream of the GST coding region into the EcoRI/XhoI restriction enzymes site of the expression plasmid pGEX6P3 for the expression of GST-6× histidine (6×His tag disclosed as SEQ ID NO: 13) fusion protein. This control construct for NS1 was designated pGEX6P3-6×his (6×His tag disclosed as SEQ ID NO: 13). After PCR amplification of NP and NS1, PCR products were ligated into the T/A cloning vector, pGEM-T-easy, and transformed into DH5alpha *E. coli* host. The NP and NS1 fragments were cut out from the T/A cloning vector by using restriction enzyme sets EcoRI/XhoI and EcoRI/SalI, respectively. NP and NS1 fragments were then ligated into the EcoRI/SalI and EcoRI/XhoI sites of pMAL-c2X (New England Biolab) and pGEX6P3 (Amersham) fusion protein expression vector, respectively. The constructs were designated pMAL2cNP and pGEX6P3NS1-6×his (6×His tag disclosed as SEQ ID NO: 13) for NP and NS1 expression plasmid, respectively.

Antigen production: For the production of purified recombinant MBP-NP, GST6×his (6×His tag disclosed as SEQ ID NO: 13), and GSTNS1-6×his (6×His tag disclosed as SEQ ID NO: 13) fusion proteins, pMAL2cNP and both pGEX6P3 plasmids (pGEX6P3-6×his (6×His tag disclosed as SEQ ID NO: 13) and pGEX6P3NS1-6×his (6×His tag disclosed as SEQ ID NO: 13)) were transformed into *E. coli* TB1 and BL21, respectively. The transformed cells were grown on Luria-Bertani agar plates containing 100 µg per ml of ampicillin as recommended in the instruction manual for each expression system (TB1: pMAL protein fusion and purification system instruction manual; BL21: GST fusion system handbook). *E. coli* expressing MBP or GST fusion protein were expanded by inoculating a colony to SOC (with 2 g glucose/liter) and 2× yeast extract tryptone (2×YT) broth culture medium, respectively, with 100 µg per ml of ampicillin and then induced with isopropyl β-D-1-thiogalactopyranoside (IPTG) at a final concentration of 0.5 to 1 mM when OD at 600 nm reaches 0.5 for TB1 and 2.0 for BL21, respectively. After induction, bacteria cultures were grown for 2 to 6 hours and then bacteria were pelleted by centrifugation at 2700×g for 15 min. Pellets collected from each liter of cultures were either frozen directly at −20° C. or resuspended in 25 ml of a column binding buffer (20 mM Tris-HCl [pH 7.4], 200 mM NaCl, 1 m M EDTA) supplemented with 0.1 mg/ml of Pefablock protease inhibitor (Roche) before freezing overnight.

Purification of recombinant fusion protein: Recombinant MBP-NP protein was purified in a similar way as reported by Voeten et al. (J. Clin. Micro. 36: 3527-3531 (1998)). Briefly, the MBP-NP containing TB1 bacteria suspensions were thawed under ice water temperature. The bacteria suspensions were then sonicated at full power for 2 min total with a 30-sec pulse for every 20 sec of sonication. After clarification by centrifugation at 9,000×g for 30 min, supernatant was diluted 1:5 with the column-binding buffer. Recombinant MBP-NP protein was purified from the diluted supernatant by column chromatography using amylose resin (New England Biolab) with extensive wash to remove non-specific binding on the column. Purified MBP fusion protein was eluted with the column-binding buffer containing 10 mM of maltose. The presence of recombinant protein in each preparation was confirmed by WB using anti-SIV pig serum.

Recombinant GST-6×his (6×His tag disclosed as SEQ ID NO: 13) and GST-NS1-6×his (6×His tag disclosed as SEQ ID NO: 13) fusion proteins were purified from frozen bacteria pellets collected from 1 liter of culture. Ice-cold column-binding buffer (40 ml) supplemented with 0.1 mg/ml of Pefablock protease inhibitor (Roche) was added to the frozen pellets, and the pellets were shook at 4° C. until totally resuspended. Two ml of lysozyme (10 mg/ml) were then added to the pooled suspension, and the suspension was shaken at room temperature for 20 min. Later, 400 μl of 1M $MgCl_2$ and 4 ml of Triton X-100 were added to the suspension to obtain final concentrations of $Mg^{2+}$ and Triton X-100 of 10 mM and 1% (v/v), respectively. The suspension was allowed to shake for another 10 min at room temperature and then was clarified at 27,000×g for 20 min at 4° C. Supernatant was collected, 3 ml of nickel-chelated agarose (Pierce) were added to the supernatant, and the composition was mixed overnight at 4° C. Supernatant/nickel-chelated agarose mixture was loaded into a glass column and washed with 100 ml of column-binding buffer containing 20 mM of imdazole. Recombinant protein was then eluted with an elution buffer (1×TBS, pH 7.4 [25 mM Tris, 3 mM KCl, 140 mM NaCl]; 1% of B-Per II (Pierce) and 250 mM imidazole) and kept at 4° C. The presence of respective recombinant NP and NS protein in each preparation was confirmed by WB using anti-SIV pig serum.

Concentrations of each purified recombinant NP and NS1 proteins were determined with DC™ Protein Assay (Bio-Rad, Hercules, Calif., USA).

In view of the above, the present invention also provides a fusion protein. One fusion protein comprises NS1 and GST. Another fusion protein comprises NP and MBP. It will be understood by one of ordinary skill in the art that other fusion proteins can be generated in accordance with methods known in the art.

ELISA: An indirect ELISA was established using a published standard protocol with modifications. Recombinant proteins were diluted in 0.2 M carbonate-bicarbonate coating buffer [pH 9.4] and added to the ELISA plate (Dynex Technologies (Chantilly, Va.); immulon II). In brief, MBP-NP and MBP (New England BioLab) were coated onto a 96-well ELISA plate with 50 ng per well in 50 μl volume, while GSTNS1-6×his (6×His tag disclosed as SEQ ID NO: 13) and GST-6×his (6×His tag disclosed as SEQ ID NO: 13) were coated at a concentration of 100 ng/well and 50 μl volume per well for overnight at 4° C. Plates were washed with phosphate-buffered saline (PBS) containing 0.1% Tween 20 (PBST) and blocked with 1×PBS with 10% skim milk powder by incubating at 37° C. for 1 h. After blocking, plates were washed with PBST again and were ready for binding of specific antibody from pig serum.

For the detection of NP-specific antibody, serum samples were diluted 1:100 in PBST (0.1% Tween 20) and added in duplicate into the wells that were coated with MBP-NP and negative control MBP. Serum samples used for the detection of NS1 antibody were diluted 1:100 in PBS containing 0.1% Tween 20, 1% skim milk and 1% crude BL21/GST6×his (6×His tag disclosed as SEQ ID NO: 13) bacteria cell lysates and added in duplicate into wells that were coated with GST fusion protein. The crude bacteria cell lysates were prepared by resuspending each gram of bacteria pellet in 1 ml of a Tris lysis buffer (10 mM Tris, 0.04% CHAP, 0.15M NaCl, 0.0001% aprotinin and 1 mM EDTA [pH8.0]) and incubated 2 h at 4° C. on a shaking plateform. After lysis and shaking, bacteria lysates were used directly for serum dilution or kept at −80° C. until needed. After addition of diluted serum samples, the ELISA plates were incubated at 37° C. for 1 h and rinsed 3 times with PBST. After washing, goat anti-swine IgG or IgM antibodies (KPL) were added and incubated at 37° C. for 1 h. Specific antigen-antibody reaction was visualized by adding TMB microwell substrate (KPL) and incubated for 15 min at ambient temperature. Colorimetric reaction was stopped by adding an equal volume of 1 N HCl. Then, plates were read at a wavelength of 450 nm in a ELISA plate reader.

HI test: HI test was performed by using a standard protocol based on the procedure recommended by the Centers for Disease Control (Concepts and procedures for laboratory-based influenza surveillance). Serum samples collected from H1N1 infection were tested for HI activity against 4 different H1N1, while H3N2-infection was tested by using one H1N1 and two H3N2 SIV. HI antibody titer of each sample was determined as the reciprocal of highest dilution in which no HA was observed. Samples with no HI activity at dilution higher than 1:10 were considered negative for HI antibody.

WB assay: Purified NP, NS1 and the control fusion protein antigens were detected with anti-SW polyclonal pig sera by WB assay. MBP (1 μg), MBP-NP (1 μg), GST-6×his (6×His tag disclosed as SEQ ID NO: 13) (1 μg) and GST-NS1-6×his (6×His tag disclosed as SEQ ID NO: 13) (0.8 μg) purified proteins were mixed with a denaturing sample buffer and separated by SDS-PAGE and blotting onto nitrocellulose (NC) membrane. NC membranes were then stained with ponceau S dye (0.5% wt/v Ponceau S in 1% v/v acetic acid) to visualize total proteins on blot transfer membranes, and then dye was stripped away by washing the membranes in 20 mM Tris-buffered saline (TBS). Before antibody staining, NC membranes were blocked with TBS containing 10% skim milk. MBP and MBP-NP proteins were stained with anti-SW polyclonal pig serum diluted 1:400 in TBS with 0.1% Tween 20 (TBST, pH 7.5) for 1 h at room temperature. After washing 3 times with TBST, NC was stained with TBST containing 50 ng/ml of horseradish peroxidase (HRP)-conjugated protein G. NC membrane, which blotted with GST fusion, was stained with anti-SW polyclonal pig serum that had been pre-absorbed with BL21 lysate for 1 h at 37° C. Pig serum pre-absorption was done by incubation of serum (1:400 dilutions) with BL21 lysate buffer (TBS with 0.1% Tween 20, 1% skim and 1% BL21/GST-6×his (6×His tag disclosed as SEQ ID NO: 13) bacteria cell lysates) at 37° C. for 1 h. After incubation, pre-absorbed serum were cleared by centrifuge at 2,700×g for 15 min at room temperature before use for staining. Pig antibodies bound on the membrane were detected with goat anti-swine IgG antibodies that conjugated with HRP. HRP signals on the membrane were then developed with TMB substrate buffer (KPL).

Cutoff determination: 19 and 16 pigs were infected with H1N1 and H3N2, respectively, and 13 pigs were used for negative control. Positive serum samples (n=99) were collected from experimentally SIV-infected pigs collected at 1, 2 and 3 or 4 week post-infection. Sera (n=48) from 48 individual pigs on day 0 (before infection) served as the negative group sera. Positive and negative serum samples were tested in the UdELISA. $OD_{450}$ readings were obtained for analysis with GRAPH ROC software for the potential cutoff values.

Statistical analysis: OD reading or S/P ratio data collected from UdELISA and commercial H1N1 ELISA testing on serum samples collected at different time point (0, 7, 14 and 21 or 28 days PI) from sera of infected and control animals were analyzed with one-way ANOVA and Tukey methods to access the specificity and sensitivity of the detection methods used. Student's t-test was used for the comparison of the anti-NP or NS1 IgG level between infected and vaccinated group.

Cloning and expression: SIV NP and NS1 protein coding regions were successfully cloned into the expression vectors pMAL2cx and pGEX6p3, respectively, which were confirmed with sequencing data. MBP-NP, GST-6×his (6×His tag disclosed as SEQ ID NO: 13) and GST-NS1-6×his (6×His tag disclosed as SEQ ID NO: 13) were purified by affinity chromatography using amylose or nickel-coated agarose. Purified recombinant MBP-NP and GST-NS1 were successfully detected with anti-SIV pig serum, while MBP or GST tag alone was not stained. The detected fusion form of NP and NS1 have a size of around 100 and 50 kDa, respectively.

Determination of the cutoff value, sensitivity, and specificity: To determine the cutoff value between negative and positive results, 48 serum samples from naïve young pigs, which were never exposed to SIV before, and 99 serum samples collected from 22 pigs infected with either H1N1 or H3N2 at different time points after infection were tested by UdELISA. All serum samples collected from naïve pigs were negative for HI assay. After testing with UdELISA on the above samples, ROC curves generated for NP and NS ELISA had a cutoff value of 0.3 and 0.15 $OD_{450}$ values, respectively. The NP ELISA had a sensitivity and specificity of 99% and 91.7%, respectively, while NS ELISA had a sensitivity of 92.9% and specificity of 97.9%, respectively.

Validation of UdELISA: The detection of anti-NP and anti-NS1 IgG response on sera collected from non-infected, infected and vaccinated pigs by using UdELISA was evaluated. For NP antibody response, sera collected from infected pigs at different time points were tested by UdELISA and compared to a commercial H1N1 indirect ELISA (iELISA) kit. All positive sera used for validation had been detected with HI assay and had the geometric mean HI titers range from 1:320 to 640, while negative sera tested as negative by HI assay using at least four different reference H1N1 SIV strains (Table 5, below). In addition, all serum samples were also tested with a commercial H3N2 indirect ELISA kit to rule out samples that were positive for H3N2 subtypes (Table 6, below). As shown in Table 5, both assays show similar sensitivity in detecting samples collected from late time points of Sly infection (28 days PI) (15 positive vs. 0 negative), while UdELISA also had good sensitivity on HI-positive serum samples collected from early time points (7 and 14 days PI). Compared to the commercial ELISA, the UdELISA with a cutoff value of 0.3 $OD_{450}$ had only one false negative from 35 HI-positive serum samples collected at 7 to 14 days PI, while most samples (23 out of 35) were detected as false negative when tested with the commercial H1N1 ELISA assay. For the negative sera tested, the UdELISA got 2 false positives out of 60 serum samples, while the commercial ELISA had one false positive detected out of 60 negative serum samples. Comparison of NP antibody levels between the infected and vaccinated groups also showed significantly different results (P<0.05 by t-test; 0.9 vs: 0.53) (Table 7, below). Both infected and vaccinated groups showed significant differences in anti-NP antibody levels when compared to naïve animals (P<0.05). UdELISA also detected negative results on most of the serum samples collected from animals vaccinated with either one of the two commercial bivalent SIV vaccines (Table 7). As shown in Table 7, five out of 74 serum samples collected from vaccinated animals showed positive anti-NS results. In contrast, all sera samples (25 out of 25) collected from animals infected for 21 to 28 days showed positive anti-NS antibody OD readings. There is a significant difference in the mean NS antibody level generated between infected and vaccinated animal groups (1.1 vs 0.07 mean OD; P<0.0001 by t-test). Vaccinated and naïve animals had no difference in the mean OD reading for the NS antibody level (0.07 vs 0.07) (Table 7).

Comparison among UdELISA, commercial H1N1 indirect ELISA kit and HI assay: Sera collected from H1N1-infected and control pigs were test in UdELISA and a commercial H1N1 indirect ELISA. For UdELISA, a significant difference in the mean anti-NP IgG antibody level (P<0.001) was detected between infected and control groups at all time points except day 0. There is no significant difference in the mean anti-NP IgG level between 7 and 14 days PI samples (P>0.05) collected from infected pigs. By 28 days PI, anti-NP IgG levels significantly increased from what had been detected on 7 and 14 days PI (P<0.001). In contrast, the anti-NP IgM level peaked at 7 days PI and is significantly higher (P<0.001) than any other time points tested. When reaching 14 days PI, the mean anti-NP IgM level dropped and was similar to the level before infection. For the mean anti-NS IgG level, there was a similar increase in the antibody level at the early time point of the infection (7 and 14 days PI). When reaching 28 days PI, the anti-NS response significantly increased from the level detected on 7 and 14 days PI (P<0.001). Comparing to UdELISA, the detection of the same panels of sera with the commercial H1N1 indirect ELISA kit showed significant increases in anti-SIV antibody levels over every time point. However, samples collected at the early time point (7 days PI) have antibody levels not significantly different from the control serum samples. Testing of sera collected from both H1N1- and H3N2-infected pigs showed a significant increase in the overall anti-NP IgG level at each time point (P<0.001). However, there was no significant difference (P>0.05) on the mean anti-NS IgG level between sera samples collected on 7 and 14 days PI from infected pigs. By 28 days PI, the mean anti-NS level was increased significantly from the level detected on 7 and 14 days PI. For the HI assay with 7 different SIV reference strains, a high level of sensitivity was noticed at an early time point for H1N1 samples, while H3N2 samples peaked at 14 days PI. Thus, there appeared to be a more rapid increase in anti-NP antibody in H3N2-infected pigs when compared to H1N1-infected pigs, while the induction of anti-NS responses was similar between these two subtypes. All inoculated animals had HI antibody only to the respective subtype of SIV inoculum on 7 days PI, and antibody titers ranged from 1:320 to 1:640. All pigs were still seropositive (1:160-1:320) at the termination of the study (28 days PI for H1N1 and 21 days PI for H3N2). All vaccinated animals were positive for HI antibody against SIV of both subtypes (i.e., H1 and H3). HI titers induced by vaccination detected at 4 weeks after the first vaccination and at 2 weeks after second-dose vaccination ranged from 1:40 to 1:5120.

Validation: The cutoff values for the UdELISA assay were determined, and a good separation of infected and non-infected animals can be achieved based on their anti-NP and NS antibody levels. Most of the serum samples collected from infected animals (H1N1 and H3N2) showed a high level of anti-NP and NS1 response, and the mean antibody levels were significantly different from control animals or before infection (P<0.001) (Table 7). According to the ROC curves, the anti-NP responses were detected with high sensitivity (99%) and an acceptable specificity of 91.7%. In contrast, anti-NS responses were detected with high specificity but lower sensitivity. Since anti-MBP antibody can be detected in pig serum, it may be necessary to include bacteria lysates and MBP protein in the antibody buffer to improve the specificity of the anti-NP antibody detection. On the other hand, even when the specificity for NS1 detection was high, false positive cases still existed in sera collected from vaccinated samples when a cut off value was set at 0.15 ($OD_{450}$) (Table 7). No significant difference in the mean anti-NS IgG level was detected by UdELISA between vaccinated and unvaccinated naïve pig serum samples (P>0.05; Table 7), demonstrating that NS1 antibody levels were not affected by vaccination, except in a few individual animals. As mentioned above, NS2 have been identified in the virion of SIV, and they share the same N terminus with NS1. Therefore, the removal of the common N-terminal region from the NS1 target antigens or use of GST-NS2-6xhis (6xHis tag disclosed as SEQ ID NO: 13) as control antigens may help to reduce the number of false positive cases in differential diagnosis. As shown in Table 7 there is a significant difference (P<0.05) in the mean anti-NP levels between vaccinated and infected animals.

The quantitative and qualitative comparisons demonstrated that UdELISA is a better alternative to the commercial indirect ELISA or HI assay on SIV serology. The UdELISA method is as sensitive as the commercial indirect ELISA method for detecting anti-NP antibodies in pig sera from 28 days PI samples (Table 5). And as shown in Table 5, HI-positive serum samples can be detected by UdELISA early in the infection (7 days PI; anti-NP IgG level) with much less false negative cases (Table 5) than the commercial H1N1 indirect ELISA, and the mean anti-NP and NS antibody levels are significantly different between infected and control groups. In contrast, the commercial H1N1 indirect ELISA test with a cut-off value at 0.4 (S/P ratio) cannot pick up most of the HI-positive serum samples at 7 and 14 days PI (Table 5), but it has a slightly better false positive rate (1 out of 60 and 2 out of 60 for commercial indirect ELISA and UdELISA, respectively) than the UdELISA assay when detecting sera collected from animals that were never exposed to SIV (Table 5). If the cut-off value for the commercial H1N1 indirect ELISA kit is adjusted to 0.1 (S/P ratio), the overall sensitivity and specificity of the assay can be improved. However, for early time-point samples (7 days PI) there is no significant difference (P>0.05) in the mean anti-H1N1 antibody levels between infected and control groups. One of the possible reasons may be because the kit was designed to focus on detecting antibodies against the H1N1 subtype only. An S/P ratio set too low may have a higher chance to detect antibodies that cross-react with other subtypes. For the purpose of preliminary surveillance of herd immunity and vaccination timing, it may not be necessary to expend too much effort determining the specific circulating subtypes in the first place; alternatively, the use of UdELISA, which provides universal detection, should meet this need and then HI can be used for the follow-up subtyping. When compared to HI, UdELISA provides high throughput and subtype-unrestricted detection of anti-NP and NS antibody responses. The peak of detection of anti-SIV by HI are 7 days PI and 14 days PI for H1N1 and H3N2, respectively. These are similar to the anti-NP IgM antibody levels, which peak early after SIV infection. Therefore, simultaneous detection of anti-NP IgM and IgG levels in the UdELISA can provide an even more sensitive universal detection method for sera collected from animals that have been infected for short periods of time.

The present invention provides a simple, reliable, low-cost, and robust test for the detection and differentiation of SIV infection in pigs. It represents a valuable addition to SIV serology that will be useful for routine diagnostics, epidemiological surveys, and design of marker vaccines.

TABLE 5

| | No. of serum samples | | | | |
|---|---|---|---|---|---|
| | From infected pigs[b] | | | | From non- |
| Assay[a] | 7 dpi (n = 19) | 14 dpi (n = 17) | 28 dpi (n = 15) | overall (n = 51) | infected pigs (n = 60)[c] |
| UdELISA (NP) positive | 18 | 17 | 15 | 50 | 2 |
| UdELISA (NP) negative | 1 | 0 | 0 | 1 | 58 |
| Commercial H1N1 iELISA positive | 0 | 12 | 15 | 27 | 1 |
| Commercial H1N1 iELISA negative | 18 | 5 | 0 | 24 | 59 |

[a]UdELISA cutoff = 0.3 ($OD_{450}$); Commercial H1N1 ELISA assay cutoff = 0.4 (S/P ratio).
[b]HI positive serum samples collected from H1N1-infected animals at 7, 14 and 28 days PI of challenge study.
[c]Day 0 and control serum samples (n = 60) collected from pigs never exposed to SIV and negative on HI assay with 4 different H1N1 isolates as reference antigens (2 atypical H1N1 isolates and 2 typical H1N1 isolates). These 60 serum samples were checked with a commercial H3N2 ELISA assay kit and were confirmed as negative.

TABLE 6

| | | | | | No. of serum samples |
|---|---|---|---|---|---|
| | From infected pigs[b] | | | | From non- |
| Assaya | 7 dpi (n = 19) | 14 dpi (n = 19) | 28 dpi (n = 10) | overall (n = 48) | infected pigs (n = 59)[c] |
| UdELISA (NP) positive | 19 | 19 | 10 | 48 | 3 |
| UdELISA (NP) negative | 0 | 0 | 0 | 0 | 56 |
| Commercial N3N2 iELISA positive | 4 | 9 | 5 | 18 | 0 |
| Commercial H3N2 iELISA negative | 15 | 10 | 5 | 30 | 59 |

[a]UdELISA cutoff = 0.3 ($OD_{450}$); Commercial H3N2 ELISA assay cutoff = 0.4 (S/P ratio).
[b]HI positive serum samples collected from H3N2-infected animals at dpi 7, 14 and 21 days of challenge study.
[c]Day 0 and control serum samples (n = 59) collected from pigs never exposed to SIV and negative on HI assay with 2 different H3N2 isolates (A/Sw/IA/41305/98 and A/Sw/NC/35922/98 as reference antigens. These 59 serum samples were checked with a commercial H1N1 ELISA assay kit and were confirmed as negative.

TABLE 7

| Detection of NP and NS antibodies in naïve, infected or vaccinated pigs | | | | | | |
|---|---|---|---|---|---|---|
| Naïve young pigs§ | | | 21 to 28 days post-infection or vaccination‡ | | | |
| HI* (+/total) | SIV protein | UdELISA†(no. of + sera /total) | Treatment | HI (+/total) | SIV protein | UdELISA (no of + sera /total) |
| 0/41 | NP | 0.13 (1/41) | Infection | 25/25 | NP | 0.9 (25/25) |
| | | | Vaccination | 92/94 | | 0.52 (79/94) |

TABLE 7-continued

Detection of NP and NS antibodies in naïve, infected or vaccinated pigs

| Naïve young pigs§ | | | 21 to 28 days post-infection or vaccination‡ | | | |
|---|---|---|---|---|---|---|
| HI*<br>(+/total) | SIV<br>protein | UdELISA†(no.<br>of + sera /total) | Treatment | HI<br>(+/total) | SIV<br>protein | UdELISA (no<br>of + sera /total) |
| | NS | 0.07 (1/41) | Infection<br>Vaccination | 25/25<br>92/94 | NS | 1.1 (25/25)<br>0.05 (5/94) |

§HI and UdELISA assay using serum samples (n = 41) collected from 41 naïve pigs on day 0 before infection showed negative HI titer (H1N1 infection group use 4 different H1N1 reference antigens; H3N2 group use both H1N1 IA and 2 H3N2 reference antigens [IA and NC H3N2]). In addition, all sera were checked with a commercial H3N2 indirect ELISA kit as negative (0.4 S/P ratio as cutoff).
‡HI and UdELISA assay using serum samples (n = 119) collected on 21 or 28 days PI or vaccination from 25 infected and 94 vaccinated pigs.
*HI cutoff: >1:10.
†Mean $OD_{450}$ readings with cutoff = 0.3 for NP; 0.15 for NS ($OD_{450}$).

Other references include: Birch-Machin et al., J. Virol. Methods 65: 225-263 (1997); Bucher et al., J. Clin. Microbiol. 29: 2484-2488 (1991); Cretescu et al., Infect. Immun. 22: 322-327 (1978); Hilbrands et al., Proceedings of the 35th Annual Meeting of the American Association of Swine Veterinarians, Des Moines, Iowa, 2004, pp. 63-65; Inoue, J. Gen. Virol. 73: 2151-2154 (1992); Jackson et al., Proceedings of the 35th Annual Meeting of the American Association of Swine Veterinarians, Des Moines, Iowa, 2004, pp. 235-240; Kapaklis-Deliyannis et al., Electrophoresis 14: 926-936 (1993); Khristova et al., Acta. Virol. 32: 109-116 (1988); Nakajima et al., Virus Genes 4: 5-13 (1990); Nakajima et al., Virus Genes 4: 15-26 (1990); Neitzert et al., Virol. 184: 799-804 (1991); Ozaki et al., Vet. Microbiol. 82: 111-119 (2001); Richardson et al., Arch. Virol. 116: 69-80 (1991); Schild et al., Nature 303: 706-709 (1983); Skehel, Virol. 49: 23-36 (1970); and Webster et al., Infect. Immun. 17: 561-566 (1977).

All references cited herein are hereby incorporated by reference in their entireties.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention, unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A universal and differential assay kit for the detection of swine influenza virus (SIV) in a biological sample, which kit comprises isolated or purified SIV non-structural 1 (NS1) protein, optionally as part of a fusion protein, and isolated or purified SIV nucleoprotein (NP), optionally as part of a fusion protein.

2. The kit of claim 1, wherein NS1 protein is part of a fusion protein with glutathionine-S-transferase (GST).

3. The kit of claim 1, wherein NP is part of a fusion protein with maltose binding protein (MBP).

4. The kit of claim 1, wherein SIV NS1 protein and SIV NP are immobilized on a solid support.

5. The kit of claim 1, which further comprises a first indicator reagent comprising an anti-swine IgG antibody and a second indicator reagent comprising an anti-swine IgM antibody.

6. The kit of claim 5, wherein the first indicator reagent comprises a first detectable label and the second indicator reagent comprises a second detectable label, which can be the same or different.

* * * * *